United States Patent [19]

Pettit et al.

[11] Patent Number: 5,430,053
[45] Date of Patent: Jul. 4, 1995

[54] ISOLATION AND STRUCTURE OF DICTYOSTATIN 1

[75] Inventors: George R. Pettit, Paradise Valley; Zbigniew A. Cichacz, Phoenix, both of Ariz.

[73] Assignee: Arizona Board of Regents acting on behalf of Arizona State University, Tempe, Ariz.

[21] Appl. No.: 229,658

[22] Filed: Apr. 19, 1994

[51] Int. Cl.[6] ............................................. A61K 31/335
[52] U.S. Cl. ..................................... 514/450; 549/271
[58] Field of Search ............................ 549/271; 514/450

[56] References Cited

U.S. PATENT DOCUMENTS

| | | | |
|---|---|---|---|
| 4,626,547 | 12/1986 | Omura et al. | 514/450 |
| 4,686,299 | 8/1987 | Liu et al. | 549/271 |
| 4,996,229 | 2/1991 | Moore et al. | 514/450 |
| 5,091,411 | 2/1992 | De Kany et al. | 549/271 |
| 5,306,716 | 4/1994 | Holt et al. | 514/450 |

OTHER PUBLICATIONS

Boyd, M PPO Updates vol. 3 No. 10 pp. 1-12 1989.

Primary Examiner—C. Warren Ivy
Assistant Examiner—A. A. Owens
Attorney, Agent, or Firm—Richard R. Mybeck

[57] ABSTRACT

A new-type of macrocyclic lactone denominated "dictyostatin 1" bearing a 22-membered ring system is isolated from a Republic of Maldives marine sponge in the genus Spongia sp. and found to strongly inhibit the growth of an important selection of U.S. National Cancer Institute human cancer cell system and the murine P388 lymphocytic leukemia (PS $ED_{50}$ $3.8 \times 10^{-4}$ mg/ml). Dictyostatin 1 has the following structure:

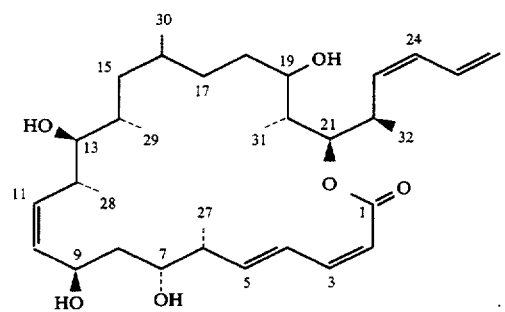

10 Claims, No Drawings

ISOLATION AND STRUCTURE OF DICTYOSTATIN 1

INTRODUCTION

The present invention relates to the discovery and isolation of new and extremely potent constituent of an Eastern Indian Ocean marine sponge of the genus Spongia sp. herein denominated "dictyostatin 1". This new macrocyclic lactone bearing a 22-membered ring system was found to be remarkably potent and specific against a number of human cancer cell lines in the U.S. National Cancer Institute's panel and to strongly inhibit growth of the murine P388 lymphocytic leukemia. Some of the work described herein was supported by PHS Grant CA-16049-07-12, awarded by the NCI Division of Cancer Treatment. The United States government may have certain rights to this invention.

BACKGROUND OF THE INVENTION

A great number of ancient marine invertebrate species in the Phyla Bryozoa, Mollusca and Porifera were well established in the earth's oceans over one billion years ago. Certainly such organisms have explored trillions of biosynthetic reactions in their evolutionary chemistry to reach present levels of cellular organization, regulation and defense. Marine sponges have changed minimally in physical appearance for nearly 500 million years, suggesting a very effective chemical evolution in response to changing environmental conditions for at least that time period. Some recognition of the potential for utilizing biologically potent marine animal constituents was recorded in Egypt about 2,700 BC, and by 200 BC sea hare extracts were being used in Greece for medicinal purposes. Such considerations, combined with the general observation that marine organisms (especially invertebrates and sharks) rarely develop cancer, led to the first systematic investigation of marine animal and plant anticancer constituents.

By 1968 ample evidence had been obtained, based on the U.S. National Cancer Institute's key experimental cancer systems, that certain marine organisms would provide new and structurally novel antineoplastic and/or cytotoxic agents. Analogous considerations suggested that marine organisms could also provide effective new drugs for other severe medical challenges, such as viral diseases. Furthermore, marine organisms were expected to contain potentially useful drug candidates (and biochemical probes) of unprecedented structural types, that would have eluded discovery by contemporary techniques of medicinal chemistry. Fortunately, some of these expectations have been realized in the intervening period. Illustrative of these successes are the discoveries of the bryostatins, dolastatins, and cephalostatins by the Cancer Research Institute at Arizona State University in Tempe, Ariz. where several members of these series of remarkable anticancer drug candidates are either now in human clinical trial or preclinical development. See U.S. Pat. Nos. 4,816,444, 4,833,257, 4,873,245, and 4,879,278.

As is well known to those presently engaged in medical research, the time between the isolation of a new compound, and its introduction to the market place takes at least several years in the best case and can take several decades. Consequently, industry, in association with the government, has devised a number of qualifying tests which serve two purposes. One purpose is to eliminate those substances whose results in the qualifying tests unequivocally demonstrate that the further expenditure of funds on developing those substances would be economically counter-productive. The second, and more important purpose, is to identify those substances which demonstrate a high likelihood of success and therefore warrant the requisite further investment necessary to obtain the data which is required to meet the various regulatory requirements imposed by those governments which regulate the market place into which such substances will enter.

The present cost of obtaining such data approaches Ten Million Dollars ($10,000,000 U.S.) per substance. Economics dictate that such an investment not be made unless there is a reasonable likelihood that it can be recovered. Absent such an opportunity, there will be no such investment, and without investment, the research requisite for the discovery of potentially life saving drugs will stop.

Only two hundred years ago, many diseases ravaged humankind. Many of these diseases now have been controlled or eradicated. In the development of the means to treat or control these diseases, work with the appropriate common experimental animals was of critical importance. With the various types of cancers, and with the HIV virus, such work is presently ongoing. The research for the treatment of various types of cancer is coordinated in the United States by the National Cancer Institute (NCI). NCI, as a government entity, has been charged with assisting, inter alia, anti-cancer research. To determine whether a substance has anti-cancer activity, NCI has established a variety of protocols, one of which involves testing the candidate substance against a cell line panel containing 60 human tumor cell lines. This protocol has been verified and is generally accepted throughout the scientific community. This protocol and the established statistical means of evaluating the results obtained therefrom have been fully described in the literature. See *Principles & Practice of Oncology* PPO Updates, Volume 3, Number 10, October 1989, by Michael R. Boyd, M.D., Ph.D., for an in depth description of the test protocol. The statistical analysis of the test protocol is explained in "Display and Analysis of Patterns of Differential Activity of Drugs Against Human Tumor Cell Lines: Development of Means Graph and COMPARE Algorithm" *Journal of the National Cancer Institute* Reports Vol. 81, No. 14, Pg. 1088, Jul. 14, 1989, by K. D. Paull et al. The context of both of these references is specifically incorporated herein by this reference thereto.

The Constitution of the United States (Art. 1, Sec. 8) authorizes Congress to establish the United States Patent and Trademark Office (USPTO) to promote scientific advancement. This obligation can only be fully met when the USPTO accepts current medical and scientific realities in the area of medical research.

The Framers of the Constitution meant to advance scientific advancement. Cells are alive. The impairment of human tumor cell growth is utility. The sole right obtained from the grant of Letters Patent is the right to prevent others from exploiting the subject matter of the patent. The recognition of cell line data as a measure of antineoplastic activity and therefor an acceptable showing of "utility" can aid research in the United States, and thereby save the citizens of the United States from being held hostage by foreign governments or foreign corporations, if such research is no longer viable in the United States.

Numerous compounds have been discovered which demonstrate significant antineoplastic activity. As discussed above, many of these compounds have been extracted, albeit with great difficulty, from living creatures such as the sponge or the sea hare. However, once the isolation and testing of such compounds has progressed, a practical problem exists, namely, how to obtain a significant quantity of the compound.

Unlike cinchona bark which is collected to produce quinine and has an excellent yield, the collection and processing of the compounds of the present invention in the natural occurring state ranges from the grossly impractical to the utterly impossible. Even ignoring potential ecological effects, the population of such creatures is clearly insufficient. Accordingly, the elucidation of the absolute structure of such antineoplastic compounds is essential.

A major component of vigorous efforts for over two decades has been directed at marine sponge antineoplastic and/or cytotoxic biosynthetic products and it is toward the furtherance of that effort that the present invention is directed.

BRIEF SUMMARY OF THE INVENTION

Marine Porifera in the genus Spongia (Family Spongiidae, Order Dictyoceratida, Class Demospongiae) have proven to be good sources of tetracyclic diterpenes. However, based on previous investigations, the Spongia was not seen to be a particularly attractive reservoir of antineoplastic macrocyclic lactones. However, natural products are replete with surprises. The present disclosure is predicated upon the unexpected discovery in a Spongia sp. of a unique macrocyclic lactone bearing a 22-membered ring system and designated "dictyostatin 1". Dictyostatin 1 possesses a remarkable structure exhibiting phenomenally potent (and selective) activity against several cell lines included in the U.S. National Cancer Institute's (NCI) panel of sixty human cancer cell lines and against murine P388 lymphocytic leukemia.

A 1988 recollection (400 kg wet wt.) of the dark brown (to black) Spongia sp. from the Eastern Indian Ocean (Republic of the Maidives), was extracted with methanol followed by methylene chloride-methanol. A methylene chloride fraction derived from the combined extract was carefully separated (guided by P388 lymphocytic leukemia bioassay) employing an extensive series of LH-20 SEPHADEX gel permeation and partition (also on SILICA GEL) chromatographic procedures followed by final isolation using reversed phase (PREPEX 5-20μ, C8 column) high performance liquid chromatography with 5:5:7 acetonitrile-methanol-water as eluent to yield (3.4×10$^{-7}$%) 1.35 mg of colorless and amorphous dictyostatin 1, mp 87°-88° C.; [α]$^{22}$D −20° (c=0.12, CH$_3$OH); UV (CH$_3$OH) λ $_{(nm, Log\ \epsilon)}$225, (4.3) 263 (4.2); IR (film) 3412, 2926, 1693, 1638, 1597, 1379, 1277, 1180, 964 cm$^{-1}$; and high resolution FAB MS, m/z 555.36621 (M+Na)$^+$ corresponding to C$_{32}$H$_{52}$O$_6$Na (calcd. mass 555.36621)

Dictyostatin 1 has the following structure:

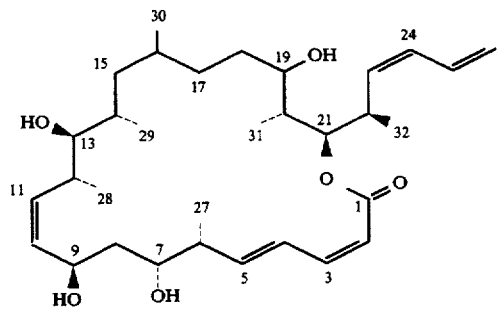

NCI data shows extremely positive results when Dictyostatin 1 is used against ovarian, CNS, renal, lung (non small cell), colon, and melanoma cells in the NCI protocol.

Accordingly, the principal object of the present invention is the isolation of a structurally unprecedented macrocyclic lactone bearing a 22 member ring and herein denominated "dictyostatin 1" having a log molar TGI$_{50}$ of about >1.0×10$^{-3}$ against various human cancer cell lines and an P388 ED$_{50}$ of 0.00038 μg/ml.

Another object of the present invention is to provide the structural elucidation of the substance denominated "dictyostatin 1".

These and still further objects as shall hereinafter appear are readily fulfilled by the present invention in a remarkably unexpected manner as will be readily discerned from the following detailed description of an exemplary embodiment thereof.

DESCRIPTION OF PREFERRED EMBODIMENTS

Dictyostatin 1 was isolated from a Spongia sp. (Porifera: Demonspongiae: Dictyoceratida: Spongiidae) and identified by taxonomist Dr. John N. A. Hooper, Curator of Porifera, Northern Territory Museum of Arts and Sciences, Darwin, NT, Australia. A museum specimen is deposited in the Arizona State University/Cancer Research Institute (ASU/CRI) collection in Tempe, Arizona as deposit M-5024, B 724908 and is preserved in alcohol. The deposit is made pursuant to ASU/CRI's CITES (Convention on International Trade in Endangered Specie of Wild Fauna and Flora) permit authorizing the Institute to receive and store preserved, dried or embedded specimens.

Dictyostatin 1, a new type of macrocyclic lactone bearing a 22-membered ring system has been isolated (3.4×10$^{-7}$% yield) from a Republic of Maldives marine sponge in the genus Spongia sp. and found to strongly inhibit growth of the murine P388 lymphocytic leukemia and various other human cancer cells in the NCI screen as hereinafter reported.

Marine invertebrates are proving, as originally predicted (See: Pettit et al., Nature, 1970, 227, 962), to be exceptionally important sources of structurally unique antineoplastic substances. Among such biosynthetic products already under preclinical or clinical development, macrocyclic lactones of the bryostatin, spongistatin and halichondrin/halistatin types provide useful illustrations. Other interesting cell growth inhibitory substances include the marine sponge jaspisamides A–C, and miyakolide, the sea pen lituarines A–C, the dinoflogellate amphidinolides, all B, G and H, incorporating 16- to 25-membered lactone rings and related open chain marine sponge constituent discodermolide.

The present disclosure is predicated upon the discovery and structural elucidation of a unique macrocyclic lactone bearing a 22-membered ring system and designated dictyostatin 1 and shown to have strong cancer cell growth inhibitory properties.

Specimens of the dark marine sponge Spongia sp. (Order Dictyoceratida, Class Demospongiae, Family Spongiidae) collected in the Republic of Maldives in 1986 and recollected (400 Kg, wet wt) in 1988 were originally employed to isolate spongistatins 1–3 in $10^{-6}$ to $10^{-8}$ yields. Further vigorous investigation of a murine P388 lymphocytic leukemia cell line (PS system) active fraction (methylene chloride derived) afforded a mixture of trace constituents from which dictyostatin 1 was isolated.

Isolation of Dictyostatin 1. Processing began with the removal of the shipping solution (methanol/sea water) from the Spongia and its partitioning with dichloromethane by the counter-current method. The dichloromethane fraction was evaporated to give a black solid (472.0 g; PS $ED_{50}$ 0.91 μg/ml). The containers were refilled with 1:1 dichloromethane/methanol. After 8–13 days the solution was removed and water (about 15%) was added to complete the separation of the dichloromethane layer from methanol/water. The dichloromethane layer was evaporated "in vacuum" (the first dichloromethane extraction) and yielded a dark brown solid (1504.1 g; PS $ED_{50}$ 4.6 μg/ml). The recovered dichloromethane was remixed with the upper methanol/water layer, methanol was added to reform a single phase and the mixture was returned to the sponge containers. After 7 days the solvent was again drained, and the solution was mixed with water (15%). The separated dichloromethane layer (second dichloromethane extraction) yielded 747.3 g (PS $ED_{50}$ 27.0 μg/ml).

The first dichloromethane extract (1504.1 g) was partitioned three times between hexane and 9:1 methanol/water. The hexane layer was discarded. The methanol/water phase was diluted to 3:2 (by addition of water) and extracted four times with dichloromethane. The dichloromethane layer was concentrated and the residue (52.45 g) showed significant PS cytostatic activity (PS $ED_{50}$ 0.24 μg/ml).

The second dichloromethane extract (747.3 g) was separately partitioned in a similar manner to the first dichloromethane extract and yielded 34.42 g (PS $ED_{50}$ 0.26 μg/ml).

The PS active dichloromethane fractions (1st and 2nd dichloromethane extraction) were combined and initially separated by gel permeation chromatography employing Sephadex LH-20 (2.7 kg, 9×130 cm) with methanol as eluent. The eluted fractions were concentrated and tested. The fraction that showed the strongest activity (13.84 g; PS $ED_{50}$ 0.011 μg/ml) was again separated using Sephadex LH-20 (1.6 kg; 8 ×110 cm) with hexane-toluene-methanol (3:1:1). The resulting active fraction (947 mg, PS $ED_{50}$ 0. 015 μg/ml) contained an inactive dark brown solid that was removed utilizing a medium pressure (to 50 psi) liquid chromatography column using Silica gel 60 (4–63 μm) and elution with solvent gradient: hexane-dichloromethane-methanol→methanol. This resulted in a significant increase in activity (40.7 mg; PS $ED_{50}$ 0.0052 μg/ml). The obtained fraction still contained a large amount of the yellow inactive ingredients with different polarities. They were removed by repeated separation (3 times) on a HPLC reverse phase column Prepex 5–20u, C8 with methanol-acetonitrile-water in varying ratios as the eluent. The resulting fraction (3.03 mg; PS $ED_{50}$ 0. 002 μg/ml) contained only one major component. It was finally purified on a HPLC reverse phase column Li-Chrospher 100 RP-18 using a mixture of acetonitrile-water (45–55) as a mobile phase to yield (3.4×$10^{-7}$%) 1.35 mg of dictyostatin 1 colorless and amorphous; P388 lymphocytic leukemia $ED_{50}$ 3.8×$10^{-4}$ μg/mL); mp 87°–88° C.; $[\alpha]^{22}_D$ −20° (c=0.12, $CH_3OH$); UV ($CH_3OH$) λ (nm, log ε) 225, (4.3) 263 (4.2); IR (film) 3412, 2926, 1693, 1638, 1597, 1379, 1277, 1180, 964 $cm^{-1}$; high resolution FAB MS, m/z 555.36621 $[M+Na]^+$ corresponding to $C_{32}H_{52}O_6Na$ (calcd mass 555.36621)

The structure of dictyostatin 1, as shown above, was primarily deduced on the basis of high field (400 and 500 MHz) 2D-NMR data that included $^1H$, $^{13}C$, APT, $^1H$-$^1H$-COSY, HMQC, HMBC, and NOE experiments. Presence of an ABX spin system in the $^1H$-NMR spectrum of dictyostatin 1 at δ5.21 (br d, 17 Hz), 5.11 (br d, 11 Hz), and 6.67 (dt, 17, 11 Hz) indicated a terminal unit. A broad singlet at δ5.10 correlating with a 13C signal at δ78.63 and a carbonyl signal at δ168.10 in the HMBC spectrum suggested a macrolide. The coupling relationships of signals corresponding to H-2, H-3, H-4 and H-5 were established and extended to H-13. Although some of the signals were obscured, coupling of H-13 to H-19 was also established and extended to H-23 and H-26. Analysis of the HMQC and HMBC spectra supported the structure shown. The signal assignments (Table 1, below) and especially those attributed to the six methyl proton signals which showed strong HMBC correlations provided below. A six-membered ring formed by bonding C-9 to C-13 was eliminated by the NOE observed between H-9 and H-12. Dreiding models illustrated that a NOE between H-9 and H-12 would not be possible if a C-9 to C-13 dihydropyran ring was present. Also, the mass spectra supported absence of a dihydropyran ring.

Table 1. NMR Assignments for Dictyostatin 1 (2) Recorded in $CD_3OD$, and coupling constants are in Hz (in parenthesis): the n and p are APT results. Mixing time for the HMBC was set at 60 microseconds.

| postn | $^{13}C$ (100 MHz) | $^1H$(400 MHz) | HMBC (500 MHz) | NOE (400 MHz) |
|---|---|---|---|---|
| 1 | 168.10p | | H-21, H-2, H-3 | |
| 2 | 118.03n | 5.52 d(11) | | |
| 3 | 144.89n | 6.62 t(11) | H-5 | H-2, H-5 |
| 4 | 128.58n | 7.17 dd(11, 16) | H-2 | H-27 |
| 5 | 146.42n | 6.14 dd(6.7, 16) | H-3, H-27 | H-3, H-7 |
| 6 | 44.05n | 2.57 brm | H-27 | H-7, H-5 |
| 7 | 70.37n | 4.02 dt(3.1, 10.7) | H-27 | H-6 |
| 8 | 40.59p | 1.47 *;1.38 * | | |
| 9 | 65.50n | 4.62 brdd(4.8, 8.7) | H-11 | H-12 |
| 10 | 134.89n | 5.37 brdd(8.7, 11) | | |
| 11 | 131.32n | 5.52 brt(11) | H-28 | |

-continued

| postn | $^{13}$C (100 MHz) | $^1$H(400 MHz) | HMBC (500 MHz) | NOE (400 MHz) |
|---|---|---|---|---|
| 12 | 35.74n | 2.72 brm | H-28, H-10 | H-9, H-13 |
| 13 | 80.37n | 3.06 dd(2.9, 8.2) | H-28, H-29 | |
| 14 | 35.32n | 1.58 * | H-29 | |
| 15 | 42.26p | 1.22 m; 0.88 m | H-29, H-30 | |
| 16 | 31.22n | 1.50 m; | H-30 | |
| 17 | 32.74p | 1.56 m; 0.68 m | H-30 | |
| 18 | 32.50p | 1.82 m; 1.08 m | | |
| 19 | 73.72n | 3.33 m | H-31 | |
| 20 | 40.82n | 1.86 m | H-31 | H-19, H-21 |
| 21 | 78.63n | 5.10 dd(5, 7)** | H-31, H-32 | H-22 |
| 22 | 35.82n | 3.13 m | H-32, H-24 | H-25 |
| 23 | 134.53n | 5.30 t(11) | H-32 | H-24, H-32 |
| 24 | 131.22n | 6.02 t(11) | H-23, H-26 | |
| 25 | 133.43n | 6.67 dt(17, 11) | H-23 | H-22 |
| 26 | 118.58p | 5.21 brd(17); 5.11 brd(11) | H-24 | |
| 27 | 13.75n | 1.11 d(7.0) | H-5 | H-4 |
| 28 | 19.35n | 1.09 d(7.1) | | |
| 29 | 15.97n | 0.92 d(6.4) | | H-13 |
| 30 | 21.81n | 0.89 d(6.5) | | H-15 |
| 31 | 10.39n | 1.03 d(6.8) | | H-21 |
| 32 | 18.06n | 0.98 d(6.7) | | |

*These are overlapping signals.
**The coupling pattern and coupling constants were measured in CD$_3$CN.

The geometry of the $\Delta^2$, $\Delta^{10}$, and $\Delta^{23}$ double bonds were assigned the cis (Z) configuration based on the 11 Hz coupling constants found for each of the respective sets of olefin hydrogen atoms. The $\Delta^4$ double bond hydrogens each exhibited a 16 Hz coupling constant. Thus the $\Delta^4$-olefin was assigned the trans (E) geometry. The NOE difference spectroscopy experiments were recorded in both CD$_3$OD and CD$_3$CN and the results shown in Table 1 (supra) favored the solution configuration depicted. Many of the single bonds in the structure are flexible. Structural elucidation of dictyostatin 1 was challenging and required in-depth, high field 400 and 500 MHz 2D NMR analyses (APT, $^1$H-$^1$H-COSY, $^1$H-$^{13}$C-COSy, HMBC, and NOE) employing acetonitrile-d$_3$, pyridine-d$_5$ and methanol-d$_3$ solvent systems. The assignments are recorded in Table 1.

Dictyostatin 1 represents the first member of a totally new series of cancer cell growth inhibitors to be discovered. Work is continuing to devise means and methods to markedly increase the availability of dictyostatin 1 through biosynthetic and/or total synthetic approaches. Increased availability of this promising substance will allow extended biological evaluations to proceed.

Dictyostatin 1 was found to be active and selective against a number of NCI human cancer cell lines, namely, NCI H460 non-small cell lung; KM 20L2 colon; SF-295 CNS; SK-MEL-5 melanoma; OVCAR-3 ovarian; and A-498 renal cancers in the NCI panel of sixty human cancer cell lines as shown in Tables II and III, below.

TABLE II pP388 RUN 00814
07/09/93 BY Lee Williams
POSITIVE CONTROL = 1.6 *

TABLE OF ED50 VALUES

| SAMPLE | ED50 (μg/ml) | $10^2$ $10^1$ $10^0$ $10^{-1}$ $10^{-2}$ $10^{-3}$ $10^{-4}$ $10^{-5}$ |
|---|---|---|
| Dictyostatin 1 | = 0.00038 | |

TABLE III

Dictyostatin 1

ASU-CRI: HUMAN TUMOR CELL LINES
RUN:R079  S-4  (07-19-1993)
2  1  0  −1  −2  −3  −4  −5

| CELL TYPE | CELL-LINE | GI-50 (μG/ML) |
|---|---|---|
| Ovarian | OVCAR-3 | > 1.0 × 10 −3 |
| CNS | SF-295 | = 2.4 × 10 −4 |
| Renal | A498-3 | = 4.0 × 10 −4 |
| Lung-NSC | NCI-H460 | = 5.5 × 10 −5 |
| Colon | KM20L2 | = 3.2 × 10 −4 |
| Melanoma | SK-MEL-5 | = 4.8 × 10 −4 |

TABLE III-continued

| CELL TYPE | CELL-LINE | TGI (μG/ML) |
|---|---|---|
| Ovarian | OVCAR-3 | $> 1.0 \times 10^{-3}$ |
| CNS | SF-295 | $> 1.0 \times 10^{-3}$ |
| Renal | A498-3 | $> 1.0 \times 10^{-3}$ |
| Lung-NSC | NCI-H460 | $= 3.8 \times 10^{-4}$ |
| Colon | KM20L2 | $> 1.0 \times 10^{-3}$ |
| Melanoma | SK-MEL-5 | $> 1.0 \times 10^{-3}$ |

| CELL TYPE | CELL-LINE | LC-50 (μG/ML) |
|---|---|---|
| Ovarian | OVCAR-3 | $> 1.0 \times 10^{-3}$ |
| CNS | SF-295 | $> 1.0 \times 10^{-3}$ |
| Renal | A498-3 | $> 1.0 \times 10^{-3}$ |
| Lung-NSC | NCI-H460 | $> 1.0 \times 10^{-3}$ |
| Colon | KM20L2 | $> 1.0 \times 10^{-3}$ |
| Melanoma | SK-MEL-5 | $> 1.0 \times 10^{-3}$ |

Dictyostatin 1 can also be effectively modified with some or all of the following acids.

(a) saturated or unsaturated, straight or branched chain aliphatic carboxylic acids, for example, acetic, propionic, butyric, isobutyric, tert-butylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic-aliphatic carboxylic acids, for example, phenylacetic acid, phenylpropionic acid, phenylvaleric acid, cinnamic acid, phenylpropioplic acid and naphthylacetic acid, and the like. Suitable halo-, nitro-, hydroxy-, keto-, amino-, cyano-, thiocyano-, and lower alkoxyhydrocarbon carboxylic acids include hydrocarboncarboxylic acids as given above which are substituted by one or more of halogen, nitro, hydroxy, keto, amino, cyano, or thiocyano, or lower alkoxy, advantageously lower alkoxy of not more than six carbon atoms, for example, methoxy, ethoxy, propoxy, butoxy, amyloxy, hexyloxy, and isomeric forms thereof. Examples of such substituted hydrocarbon carboxylic acids are: mono-, di-, and trichloroacetic acid; α- and β-chloropropionic acid; α- and ν-bromobutyric acid; α- and β-iodovaleric acid; mevalonic acid; 2- and 4-chlorocyclohexanecarboxylic acid; shikimic acid; 2-nitro- 1-methyl-cyclobutanecarboxylic acid; 1,2,3,4,5,6-hexachlorocyclohexanecarboxylic acid; 3-bromo-2-methylcyclohexanecarboxylic acid; 4- and 5-bromo-2-methylcyclohexanecarboxylic acid; 5- and 6-bromo-2-methylcyclohexanecarboxylic acid; 2,3-dibromo-2-methylcyclohexanecarboxylic acid; 2,5-dibromo-2-methylcyclohexanecarboxylic acid; 4,5-dibromo-2-methylcyclohexanecarboxylic acid;5,6-dibromo-2-methylcyclohexanecarboxylic acid; 3-bromo-methylcyclohexanecarboxylic acid; 6-bromo-3-methylcyclohexanecarboxylic acid; 1,6-dibromo-3-methylcyclohexanecarboxylic acid; 2-bromo-4-methylcyclohexanecarboxylic acid; 1,2-dibromo-4-methylcyclohexanecarboxylic acid; 3-bromo-2,2,3-trimethylcyclopentanecarboxylic acid; 1-bromo-3,5-dimethylcycohexanecarboxylic acid; homogentisic acid, o-, m-, and p-chlorobenzoic acid; anisic acid; salicylic acid; p-hydroxybenzoic acid; b-resorcylic acid; gallic acid; veratric acid; trimethoxybenzoic acid; trimethoxycinnamic acid; 4,4'-dichlorobenzilic acid; o-, m-, and p-nitrobenzoic acid; cyanoacetic acid; 3,4- and 3,5-dinitrobenzoic acid; 2,4,6-trinitrobenzoic acid; thiocyanoacetic acid; cyanopropionic acid; lactic acid; ethoxyformic acid (ethyl hydrogen carbonate); malic acid; citric acid; isocitric acid; 6-methylsalicyclic acid; mandelic acid, levulinic acid; pyruvic acid; glycine; alanine; valine; isoleucine; leucine; phenylalanine; proline; serine; threonine; tyrosine; hydroxyproline; ornithine; lysine; arginine; histidine; hydroxylysine; phenylglycine; p-aminobenzoic acid; m-aminobenzoic acid; anthranilic acid; aspartic acid; glutamic acid; aminoadipic acid; glutamine; asparagine; and the like.

The administration of dictyostatin 1 and its pharmaceutically active, physiologically compatible derivatives is useful for treating animals or humans afflicted with a neoplastic disease, such as, for example, acute lymphocytic leukemia, malignant melanoma, adenocarcinoma of lung, neuroblastoma, colon carcinoma, ovarian carcinoma, hematologic malignancies and the like.

The dosage administered will be dependent upon the identity of the neoplastic disease; the type of host involved, including its age, health and weight; the kind of concurrent treatment, if any; the frequency of treatment and therapeutic ratio.

Illustratively, dosage levels of the administered active ingredients are: intravenous, 0.1 to about 40 mg/kg; intramuscular, 1 to about 50 mg/kg; orally, 5 to about 100 mg/kg; intranasal instillation, 5 to about 100 mg/kg; and aerosol, 5 to about 100 mg/kg. As used herein, mg/kg means weight of active ingredient in micrograms divided by the body weight of the host in kilograms.

Expressed in terms of concentration, an active ingredient can be present in the compositions of the present invention for localized use about the cutis, intranasally, pharyngolaryngeally, bronchially, intravaginally, rectally, or ocularly in a concentration of from about 0.01 to about 50% w/w of the composition; and for parenteral use in a concentration of from about 0.05 to about 50% w/w of the composition and preferably from about 5 to about 20% w/w.

The composition of the present invention are preferably presented for administration to humans and animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling the mixture into formed gelatin sheaths. As an adjuvant to the filling operation, a lubricant such as a talc, magnesium stearate, calcium stearate and the like can be added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

When desired, each tablet can be provided with a protective coating consisting of a sealing coat or enteric coat of shellac, a coating of sugar and methylcellulose and a polish coating of carnauba wax. Fluid unit dosage forms for oral administration such as syrups, elixirs and suspensions can be prepared wherein each teaspoonful of composition contains a predetermined amount of active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization can not be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, a fluid unit dosage form is prepared utilizing an active ingredient and a suitable pharmaceutical vehicle, preferably pyrogen free ("P.E.") water. A dry powder can be formulated when insufflation is the administration of choice.

For use as aerosols, the active ingredients can be packaged in a pressurized aerosol container together with a gaseous or liquefied propellant, for example, dichlorodifluoromethane, carbon dioxide, nitrogen, propane, and the like, with the usual adjuvants such a cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients to be employed as antineoplastic agents can be easily prepared in such unit dosage form with the employment of pharmaceutical materials which themselves are available in the art and can be prepared by established procedures. The following preparations are illustrative of the preparation of the unit dosage forms of the present invention, and not as a limitation thereof.

From the foregoing it is apparent that an invention has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended herein.

Accordingly, what is claimed is:

1. A substance denominated dictyostatin 1 and having the following structure:

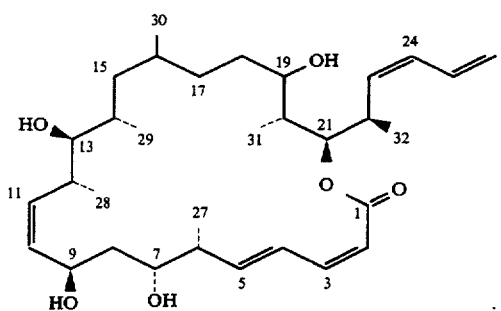

2. A substance denominated dictyostatin 1 and having the following NMR assignments when recorded in $CD_3OD$ and $CD_3CN$ with coupling constants in Hz (in parenthesis):

3. A purified composition of matter according to claim 1 wherein the concentration of said composition needed to attain an $ED_{50}$ under the P388 system is less than about $1.0 \times 10^1$ mg/ml.

4. A purified composition of matter according to claim 1 wherein the concentration of said composition needed to attain an $ED_{50}$ under the P388 system is less than $1.0 \times 10^1$ μg/ml.

5. A purified composition of matter according to claim 1 wherein the concentration of said composition needed to attain on $ED_{50}$ under the P388 system is less than $1.0 \times 10^{-1}$ μg/ml.

6. A purified composition of matter according to claim 1 wherein the concentration of said composition needed to attain an $ED_{50}$ under the P388 system is less than $1.0 \times 10^{-3}$ μg/ml.

7. A purified composition of matter according to claim 2 wherein the concentration of said composition needed to attain an $ED_{50}$ under the P388 system is less than about $1.0 \times 10^1$ mg/ml.

8. A purified composition of matter according to claim 2 wherein the concentration of said composition needed to attain an $ED_{50}$ under the P388 system is less than $1.0 \times 10^{-1}$ μg/ml.

9. A purified composition of matter according to claim 2 wherein the concentration of said composition needed to attain on $ED_{50}$ under the P388 system is less than $1.0 \times 10^{-1}$ μg/ml.

10. A purified composition of matter according to claim 2 wherein the concentration of said composition needed to attain an $ED_{50}$ under the P388 system is less than $1.0 \times 10^{-3}$ μg/ml.

* * * * *

| postn | $^{13}C$ (100 MHz) | $^1H$(400 MHz) | HMBC (500 MHz) | NOE (400 MHz) |
|---|---|---|---|---|
| 1 | 168.10p | | H-21, H-2, H-3 | |
| 2 | 118.03n | 5.52 d(11) | | |
| 3 | 144.89n | 6.62 t(11) | H-5 | H-2, H-5 |
| 4 | 128.58n | 7.17 dd(11, 16) | H-2 | H-27 |
| 5 | 146.42n | 6.14 dd(6.7, 16) | H-3, H-27 | H-3, H-7 |
| 6 | 4.05n | 2.57 brm | H-27 | H-7, H-5 |
| 7 | 70.37n | 4.02 dt(3.1, 10.7) | H-27 | H-6 |
| 8 | 40.59p | 1.47 *;1.38 * | | |
| 9 | 65.50n | 4.62 brdd(4.8, 8.7) | H-11 | H-12 |
| 10 | 134.89n | 5.37 brdd(8.7, 11) | | |
| 11 | 131.32n | 5.52 brt(11) | H-28 | |
| 12 | 35.74n | 2.72 brm | H-28, H-10 | H-9, H-13 |
| 13 | 80.37n | 3.06 dd(2.9, 8.2) | H-28, H-29 | |
| 14 | 35.32n | 1.58 * | H-29 | |
| 15 | 42.26p | 1.22 m; 0.88 m | H-29, H-30 | |
| 16 | 31.22n | 1.50 m; | H-30 | |
| 17 | 32.74p | 1.56 m; 0.68 m | H-30 | |
| 18 | 32.50p | 1.82 m; 1.08 m | | |
| 19 | 73.72n | 3.33 m | H-31 | |
| 20 | 40.82n | 1.86 m | H-31 | H-19, H-21 |
| 21 | 78.63n | 5.10 dd(5, 7)** | H-31, H-32 | H-22 |
| 22 | 35.82n | 3.13 m | H-32, H-24 | H-25 |
| 23 | 134.53n | 5.30 t(11) | H-32 | H-24, H-32 |
| 24 | 131.22n | 6.02 t(11) | H-23, H-26 | |
| 25 | 133.43n | 6.67 dt(17, 11) | H-23 | H-22 |
| 26 | 118.58p | 5.21 brd(17); 5.11 brd(11) | H-24 | |
| 27 | 13.75n | 1.11 d(7.0) | H-5 | H-4 |
| 28 | 19.35n | 1.09 d(7.1) | | |
| 29 | 15.97n | 0.92 d(6.4) | | H-13 |
| 30 | 21.81n | 0.89 d(6.5) | | H-15 |
| 31 | 10.39n | 1.03 d(6.8) | | H-21 |
| 32 | 18.06n | 0.98 d(6.7) | | |

*These are overlapping signals.
**The coupling pattern and coupling constants were measured in $CD_3CN$.